United States Patent [19]
Baker et al.

[11] Patent Number: 6,162,629
[45] Date of Patent: Dec. 19, 2000

[54] METHODS FOR PROCESSING ACTIVATED PROTEIN C

[75] Inventors: Jeffrey Clayton Baker; Andrew David Carlson, both of Indianapolis; Lihua Huang, Carmel; Theodore Arsay Sheliga, Indianapolis, all of Ind.

[73] Assignee: Eli Lilly And Company, Indianapolis, Ind.

[21] Appl. No.: 09/065,872

[22] Filed: Apr. 24, 1998

Related U.S. Application Data

[60] Provisional application No. 60/045,255, Apr. 28, 1997.

[51] Int. Cl.[7] .............................. C12N 9/96; C12N 9/48; A61K 38/48
[52] U.S. Cl. ..................... 435/212; 435/188; 424/94.64
[58] Field of Search ................... 424/94.64; 435/188, 435/212

[56] References Cited

U.S. PATENT DOCUMENTS

| | | | |
|---|---|---|---|
| 4,775,624 | 10/1988 | Bang et al. | 435/226 |
| 4,877,608 | 10/1989 | Lee et al. | 424/176.1 |
| 4,981,952 | 1/1991 | Yan | 530/384 |
| 4,992,373 | 2/1991 | Bang et al. | 435/69.6 |
| 5,093,117 | 3/1992 | Lawrence et al. | 424/1.49 |
| 5,175,087 | 12/1992 | Ranby et al. | 435/13 |
| 5,395,923 | 3/1995 | Bui-Khac et al. | 530/381 |
| 5,413,732 | 5/1995 | Buhl et al. | 252/182.11 |
| 5,478,558 | 12/1995 | Eibl et al. | 424/94.63 |
| 5,831,025 | 11/1998 | Ogata et al. | 530/380 |

FOREIGN PATENT DOCUMENTS

| | | |
|---|---|---|
| 314095 | 5/1989 | European Pat. Off. . |
| 0 445 939 | 2/1991 | European Pat. Off. . |
| 662513 | 7/1995 | European Pat. Off. . |
| 3823519 | 1/1990 | Germany . |
| 91/12320 | 8/1991 | WIPO . |
| 95/11966 | 5/1995 | WIPO . |

OTHER PUBLICATIONS

Esmon, C.T., Science, vol. 235, "The Regulation of Natural Anticoagulant Pathways", pp. 1348–1352, Mar. 1987.

Grinnell, et al., "Trans–Activated Expression of Fully Gamma–Carboxylated Recombinant Human Protein C, An Antithrombotic Factor", *Bio/Technology,* 5:1189–1192, 1987.

Yu–Chang Wang and Hanson MA (1988) "Parenteral formulations of proteins and peptides stability and stabilizers" *Journal of Parenteral Science and Technology* 42(Supplement):S3–S26.

S. A. Steiner, et al. "Stimulation of the Amidase and Esterase Activity of Activated Bovine Plasma Protein C by Monovalent Cations" *Biochemical and Biophysical Research Communications* 94(1):340–347 (May 14, 1980).

*Primary Examiner*—Jon P. Weber
*Attorney, Agent, or Firm*—Brian P. Barrett; Steve Caltrider; Doug Norman

[57] ABSTRACT

The present invention is broadly directed to a method for reducing autodegradation of activated protein C during processing and purification. The present invention provides aqueous activated protein C solutions and an improved method of processing of such solutions, comprising conducting such processing at an ionic strength of greater than 150 mM and at a pH of about 5.5 to less than 6.3.

14 Claims, 1 Drawing Sheet

METHODS FOR PROCESSING ACTIVATED PROTEIN C

PRIORITY

This application claims the benefit of U.S. Provisional application Ser. No. 60/045,255, filed Apr. 28, 1997.

FIELD OF THE INVENTION

The present invention is broadly directed to a method for reducing autodegradation of activated protein C during processing and purification.

BACKGROUND OF THE INVENTION

Protein C is a serine protease and naturally occurring anticoagulant that plays a role in the regulation of homeostasis by inactivating Factors $V_a$ and $VIII_a$ in the coagulation cascade. Human protein C is made in vivo primarily in the liver as a single polypeptide of 461 amino acids. This precursor molecule undergoes multiple post-translational modifications including 1) cleavage of a 42 amino acid signal sequence; 2) proteolytic removal from the one chain zymogen of the lysine residue at position 156 and the arginine residue at position 157 to make the 2-chain form of the molecule, (i.e., a light chain of 155 amino acid residues attached through a disulfide bridge to the serine protease-containing heavy chain of 262 amino acid residues); 3) vitamin K-dependent carboxylation of nine glutamic acid residues clustered in the first 42 amino acids of the light chain, resulting in 9 gamma-carboxyglutamic acid (GLA) residues; and 4) carbohydrate attachment at four sites (one in the light chain and three in the heavy chain). The heavy chain contains the well established serine protease triad of Asp 257, His 211 and Ser 360. Finally, the circulating 2-chain zymogen is activated in vivo by thrombin at a phospholipid surface in the presence of calcium ion. Activation results from removal of a dodecapeptide at the N-terminus of the heavy chain, producing activated protein C (aPC) possessing enzymatic activity. In concert with other proteins, activated protein C functions as perhaps the most important down-regulator of blood coagulation resulting in thrombosis.

Unfortunately, aPC can autodegrade, leading to decreased functionality as an anticoagulant. An art recognized degradation pathway for activated protein C is a proteolytic clip at the lysine residue at position 308 of the heavy chain yielding a 111 amino acid fragment. This degradation product is recognized in the art as the EAK fragment.

Previous attempts to reduce autodegradation have focused on minimizing the formation of the EAK fragment. Most notably, Prouty et al., EP 0 662 513, Jul. 12, 1995, teach minimizing autodegradation of aPC by controlling the pH to about 6.3 to 7.0; incubating the aPC in 3 M urea; or exposing aPC to extreme salt conditions, which are defined to be above 0.4 M or below 0.05 M.

Applicants have discovered a second important degradation pathway—autodegradation of the N-terminus of the light chain resulting in a clip on either side of the histidine residue at position 10. This degradation pathway yields two inactive products. The N-terminal clip of the first nine residues of the light chain yields des(1–9)activated protein C, and the N-terminal clip of the first ten residues of the light chain yields des(1–10)activated protein C. This degradation pathway, which has not been previously reported, results in loss of anticoagulant activity due to the removal of the critical GLA residues at positions 6 and 7. Therefore minimizing the level of the des(1–9)- and des(1–10)activated protein C autodegradation products is important in achieving a potent, high purity activated protein C pharmaceutical preparation. These variants were previously unknown degradation products and are exceedingly difficult, if not impossible, to remove by conventional purification techniques. The conditions to minimize their formation were previously unknown.

Identification of this important autodegradation pathway for activated protein C by Applicants has enabled the discovery of processing and formulation conditions to enhance the purity and potency of the activated protein C. Applicants have demonstrated that at a low pH (e.g. less than 6.3) the autodegradation pathway favoring the des(1–9)aPC or des(1–10)aPC predominates over the 308–309 autodegradation pathway, however use of elevated sodium chloride concentrations (greater than 150 mm) at a pH less than 6.3 substantially reduces the extent of the des(1–9)aPC and/or des(1–10)aPC autodegradation reaction.

Accordingly, the present invention provides for processing activated protein C at an ionic strength of greater than 150 mM and at a pH of about 5.5 to less than 6.3. Under these conditions the formation of des(1–9)aPC and des(1–10)aPC is significantly reduced. The present invention therefore provides an improved method for processing an aqueous solution of activated protein C without undesirable degradation.

SUMMARY OF THE INVENTION

The present invention provides aqueous activated protein C solutions and an improved method of processing such solutions, comprising conducting the processing at an ionic strength of greater than 150 mM and at a pH of about 5.5 to less than 6.3.

The invention further provides a method for purifying activated protein C by chromatographic separation, comprising eluting said activated protein C during said chromotographic separation using an aqueous elution solution having an ionic strength above 150 mM and a pH of about 5.5 to less than 6.3.

The invention further provides a method for concentrating a solution of activated protein C by filtration, comprising feeding said activated protein C to a filtration membrane as an aqueous solution having an ionic strength of greater than 150 mM and a pH of about 5.5 to less than 6.3.

The invention also provides activated protein C prepared by the processes described herein.

The invention finally provides activated protein C pharmaceutical preparations having less than 10% des(1–9)aPC and/or des(1–10)aPC by weight.

DETAILED DESCRIPTION OF THE INVENTION

Figure 1:
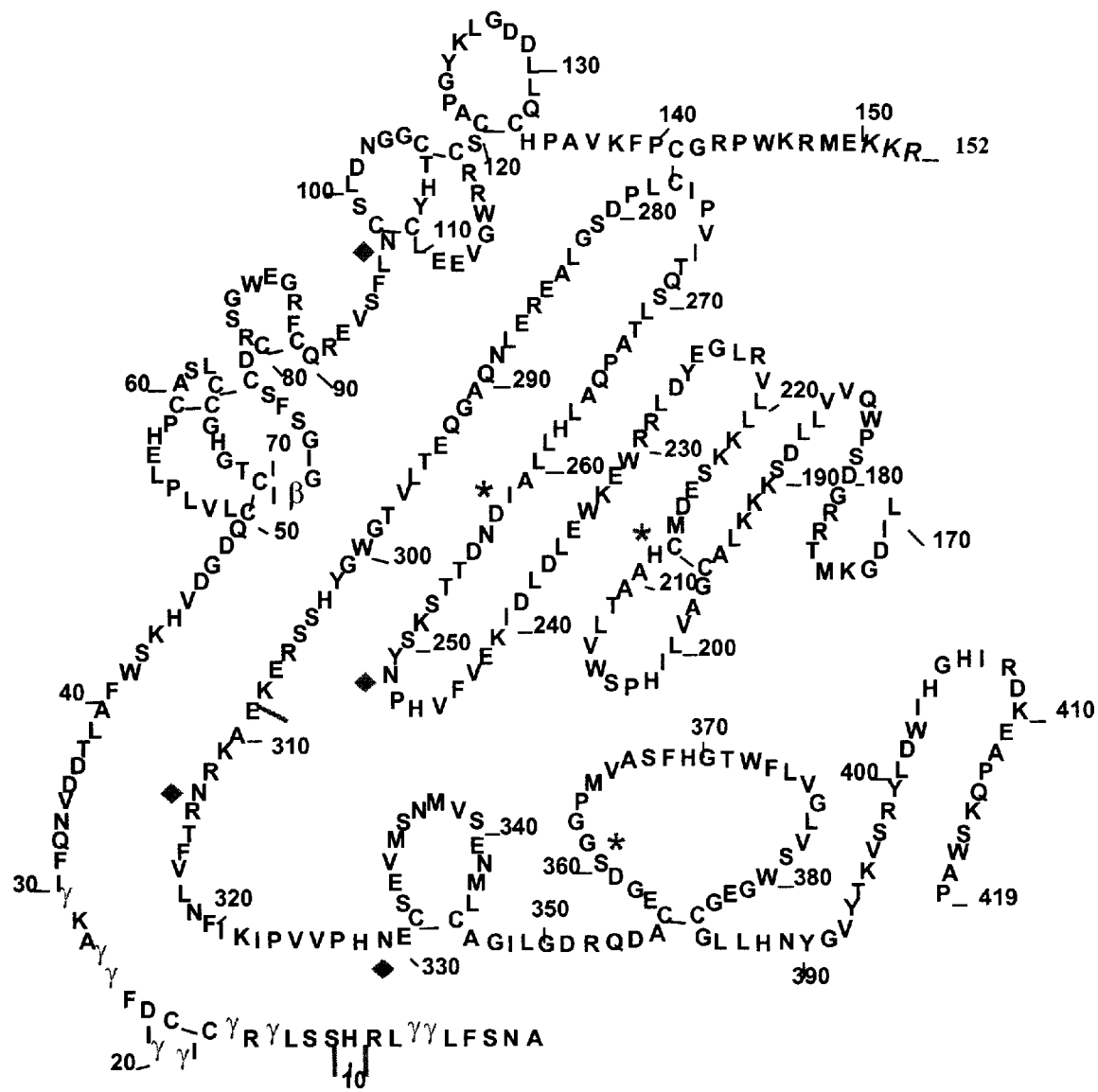
FIG. 1 provides the primary structure of activated human protein C to assist in illustrating the autodegradation pathways described herein. The nomenclature adopted herein is based on the numbering of the primary sequence of human activated protein C. One skilled in the art would recognize that other species of activated protein C may vary slightly in primary sequence thereby resulting in shifts in the nomenclature defined herein.

All amino acid abbreviations used in this disclosure are those accepted by the United States Patent and Trademark Office as set forth in 37 C.F.R. § 1.822(B)(2).

For purposes of the present invention, as disclosed and claimed herein, the following terms are as defined below.

aPC or activated protein C—refers to protein C whether recombinant or plasma derived. aPC includes and is preferably human protein C although aPC may also include other species or derivatives having protein C proteolytic, amidolytic, esterolytic, and biological (anticoagulant or pro-fibrinolytic) activities. Examples of protein C derivatives are described by Gerlitz, et al., U.S. Pat. No. 5,453,373, and Foster, et al., U.S. Pat. No. 5,516,650, the entire teachings of which are hereby incorporated by reference.

APTT—activated partial thromboplastin time.

Aqueous—includes cosolvent systems as well as use of water only as a solvent. Preferably, aqueous means water only as the solvent.

Chromatographic separation—includes chromatographic techniques recognized and appreciated in the art, including size exclusions, anionic, cationic, hydrophobic, reverse phase and the like.

Cross-flow filtration—refers to partitioning by tangential flow across a filtration membrane where the product is either retained by the membrane (as in concentration or diafiltration) or passed by the membrane (as in viral clearance filtration).

PC—protein C zymogen.

Processing—refers to unit operations useful in the manufacture of activated protein C, such as column chromatography, filtration (tangential, cross-flow, dead-end), lyophilization, pumping, or storage.

r-aPC—recombinant activated protein C produced by activating PC in vitro or by direct secretion of the activated form of protein C from procaryotic cells, eukaryotic cells, or transgenic animals including, for example, secretion from human kidney 293 cells as a zymogen then purified and activated by techniques well known to the skilled artisan and demonstrated in Yan, U.S. Pat. No. 4,981,952, and Cottingham, WO 97/20043.

The present invention relates to an improved method for processing activated protein C. The invention particularly pertains to processing activated protein C through protein enrichment or concentration and protein purification operations, while reducing autodegradation. The invention is characterized by having such processing, and especially such modification, enrichment and purification operations, conducted using an aqueous solution of the protein under the condition described herein.

The combination of conditions claimed herein minimize the formation of des(1–9)aPC and des(1–10)aPC. Des(1–9) aPC and des(1–10)aPC are exceedingly difficult to remove by known purification methodology so it is desirable to minimize their formation during manufacturing of pharmaceutical preparations of aPC. Activated protein C prepared under the claimed conditions is substantially free of des (1–9)aPC and des(1–10)aPC variants. Generally, pharmaceutical preparations of aPC prepared under these conditions are substantively free of des(1–9)aPC and des(1–10)aPC, generally having less than 10%, preferably less than 8%, more preferably less than 5%, and most preferably less than 3% of these variants, individually or in combination, by weight. The lyophilized pharmaceutical formulations prepared using aPC prepared as described and claimed herein demonstrate improved stability in the solution state (prior to lyophilizing), and 24 to 48 hours stability upon reconstitution. Not more than a 5% loss in potency is observed up to five days at 2 to 8° C., up to 50 hours at 15° C., and up to 40 hours at 25° C. Prior to the present invention, such stability was previously unachievable.

Carefully controlling the pH, ionic strength, and preferably temperature, the autodegradation of activated protein C in aqueous solutions during processing and in formulations can be reduced to levels previously unobtainable—particularly in the absences of urea or other denaturing agents, histidine, lysine hydrochloride, or albumin.

In the broad practice of the present invention, it is contemplated that processing protein C includes a wide variety of unit operations, physical separations and purification operations, including chromatographic treatment and cross-flow filtration such as for purifying the protein composition, concentrating the protein solution or for solvent exchange, as well as possibly chemical and enzymatic treatments. Protein processing contemplated by the present invention particularly includes purification by standard chromatographic methods such as ionic exchange chromatography, hydrophobic chromatography and the like, and protein concentration by ultrafiltration and similar processes. Protein processing is also intended to encompass the retention of the protein solution in holding tanks and the like preparatory to such purification and concentration steps. To reduce the instability, all processing of the activated protein C solution, including various protein purification and protein concentration steps, is conducted under the conditions described herein. Such processing steps are directed to the ultimate isolation of the protein, usually as a lyophilized powder, for formulation in a pharmaceutical preparation.

The pH of the aqueous processing solution is about 5.5 to less than 6.3. More preferably, 5.7 to less than 6.3. Still more preferably, a pH between about 5.6 to about 6.2. Even more preferred is a pH between about 5.8 to about 6.2. Still even more preferred is a pH between about 5.9 to about 6.1. The most preferred pH is about pH 6.0. Representative buffer systems to maintain effective pH control include Tris-acetate, sodium citrate, potassium citrate, citrate-glycine and sodium phosphate. More preferred buffer systems include sodium citrate and sodium phosphate. The most preferred buffer is sodium citrate. The preferred molarity of the buffer system is 10 mM to 50 mM. The most preferred molarity is 20 to 40 mM. The skilled artisan will recognize that many other buffer systems are available which also can be used to maintain the pH in the claimed range.

The ionic strength of the processing solutions is the second critical element of the present invention. Ionic strength is generally derived from the addition of pharmaceutically acceptable salts—preferably sodium chloride or potassium chloride. The ionic strength is preferably greater than or equal to 150 mM, derived from a salt concentration of greater than 150 mM in a buffered solution. Preferably, the salt concentration is no more than about 1000 mM to facilitate downstream processing. Most preferably, the salt concentration is from about 200 mm to 1000 mM. Concentrations of greater than 50 mM and below 400 mM were previously believed to be unacceptable.

An additional condition to ensure minimal autodegradation is the temperature. Preferably, the processing temperature during solution processing is between 0° C. and 10° C., more preferably 2° C. to 8° C. outside of these temperatures, significant autodegradation of activated protein C occurs. However, exceeding 10° C. for short periods of time can be tolerated without comprising the integrity of the activated protein C.

The concentration of activated protein C is not critical to the present invention. Significantly, the ability to process the protein at high concentrations is significantly enhanced under the conditions described herein. The preferred protein concentration is from about 1 mg/mL to about 50 mg/mL, more preferably 1 to 30 mg/mL, still more preferably 1 to 20 mg/mL, and most preferably 1 to 10 mg/mL, although higher or lower concentrations are considered operable.

Activated protein C prepared as described herein is useful in the treatment of a wide variety of acquired disease states involving intravascular coagulation, including thrombotic stroke, deep vein thrombosis, pulmonary embolism, peripheral arterial thrombosis, emboli originating from the heart or peripheral arteries, acute myocardial infarction, disseminated intravascular coagulation, and acute pre-or postcapillary occlusions, including transplantations or retina thrombosis.

Activated protein C is ideally formulated in the lyophilized state with a bulking agent. The bulking agent is ideally selected so that it improves the solid-state stability of the molecule. Examples of such excipients are sucrose, trehalose, and raffinose. The skilled artisan will recognize that many other bulking agents are available which also can be used in activated protein C. The bulking agent concentration of the formulation is a critical formulation variable of the freeze drying process. A preferred bulking agent is sucrose at a concentration in the solution to be lyophilized of 15 to 30 mg/mL. The most preferred concentration of sucrose in the solution to be lyophilized is 15 mg/mL in a formulation of aPC at 2.5 mg/mL. The most preferred concentration of sucrose in the solution to be lyophilized is 30 mg/mL in a formulation of aPC at 5.0 mg/mL.

The following examples are presented to illustrate and explain the invention. The scope of the invention should not be considered as being limited to these examples. Unless otherwise indicated, all references to parts and percentages are based on weight and all temperatures are expressed in degrees Celsius.

Preparation 1

Preparation of Human Protein C

Recombinant human protein C (zymogen) was produced in Human Kidney 293 cells by techniques well known to the skilled artisan such as those set forth in Yan, U.S. Pat. No. 4,981,952, the entire teaching of which is herein incorporated by reference. The gene encoding human protein C is disclosed and claimed in Bang et al., U.S. Pat. No. 4,775,624, the entire teaching of which is incorporated herein by reference. The plasmid used to express human protein C in 293 cells was plasmid pLPC which is disclosed in Bang et al., U.S. Pat. No. 4,992,373, the entire teaching of which is incorporated herein by reference. The construction of plasmid pLPC is also described in European Patent Publication No. 0 445 939, and in Grinnell et al., 1987, *Bio/Technology* 5:1189–1192, the teachings of which are also incorporated herein by reference. Briefly, the plasmid was transfected into 293 cells, then stable transformants were identified, subcultured and grown in serum-free media. After fermentation, cell-free medium was obtained by microfiltration.

The human protein C zymogen was separated from the culture fluid by an adaptation of the techniques of Yan, U.S. Pat. No. 4,981,952, the entire teaching of which is herein incorporated by reference. The clarified medium was made 4 mM in EDTA before it was absorbed to an anion exchange resin (Fast-Flow Q, Pharmacia). After washing with 4 column volumes of 20 mM Tris, 200 mM NaCl, pH 7.4 and 2 column volumes of 20 mM Tris, 150 mM NaCl, pH 7.4, the bound recombinant human protein C zymogen was eluted with 20 mM Tris, 150 mM NaCl, 10 mM $CaCl_2$, pH 7.4. The eluted protein was greater than 95% pure after elution as judged by SDS-polyacrylamide gel electrophoresis.

Further purification of the protein was accomplished by making the protein 3 M in NaCl followed by adsorption to a hydrophobic interaction resin (Toyopearl Phenyl 650M, TosoHaas) equilibrated in 20 mM Tris, 3 M NaCl, 10 mM $CaCl_2$, pH 7.4. After washing with 2 column volumes of equilibration buffer without $CaCl_2$, the recombinant human protein C zymogen was eluted with 20 mM Tris, pH 7.4. The eluted protein was prepared for activation by removal of residual calcium. The zymogen was passed over a metal affinity column (Chelex-100, Bio-Rad) to remove calcium and again bound to an anion exchanger (Fast Flow Q, Pharmacia). Both of these columns were arranged in series and equilibrated in 20 mM Tris, 150 mM NaCl, 5 mM EDTA, pH 7.4. Following loading of the protein, the Chelex-100 column was washed with one column volume of the same buffer before disconnecting it from the series. The anion exchange column was washed with 3 column volumes of equilibration buffer before eluting the protein with 0.4 M NaCl, 20 mM Tris-acetate, pH 6.5. Protein concentrations of recombinant human protein C was measured by UV 280 nm extinction $E^{0.1\%}=1.81$.

Preparation 2

Activation of Recombinant Human Protein C

Bovine thrombin was coupled to Activated CH-Sepharose 4B (Pharmacia) in the presence of 50 mM HEPES, pH 7.5 at 4° C. The coupling reaction was done on resin already packed into a column using approximately 5000 units thrombin/mL resin. The thrombin solution was circulated through the column for approximately 3 hours before adding 2-aminoethanol (MEA) to a concentration of 0.6 mL/L of circulating solution. The MEA-containing solution was circulated for an additional 10–12 hours to assure complete blockage of the unreacted amines on the resin. Following blocking, the thrombin-coupled resin was washed with 10 column volumes of 1 M NaCl, 20 mM Tris, pH 6.5 to remove all non-specifically bound protein, and was used in activation reactions after equilibrating in activation buffer.

Purified rHPC was made 5 mM in EDTA (to chelate any residual calcium) and diluted to a concentration of 2 mg/mL with 20 mM Tris, pH 7.4 or 20 mM Tris-acetate, pH 6.5. This material was passed through a thrombin column equilibrated at 37° C. with 50 mM NaCl and either 20 mM Tris pH 7.4 or 20 mM Tris-acetate pH 6.5. The flow rate was adjusted to allow for approximately 20 min. of contact time between the rHPC and thrombin resin. The effluent was collected and immediately assayed for amidolytic activity. If the material did not have a specific activity (amidolytic) comparable to an established standard of aPC, it was recycled over the thrombin column to activate the rHPC to completion. This was followed by 1:1 dilution of the material with 20 mM buffer as above.

The anticoagulant activity of activated protein C is determined by measuring the prolongation of the clotting time in the activated partial thromboplastin time (APTT) clotting assay. A standard curve is prepared in dilution buffer (1 mg/mL radioimmunoassay grade BSA, 20 mM Tris, pH 7.4, 150 mM NaCl, 0.02% $NaN_3$) ranging in protein C concentration from 125–1000 ng/mL, while samples are prepared at several dilutions in this concentration range. To each sample cuvette, 50 μL of cold horse plasma and 50 μL of reconstituted activated partial thromboplastin time reagent (APTT Reagent, Sigma) are added and incubated at 37° C. for 5 min. After incubation, 50 µL of the appropriate samples or standards are added to each cuvette. Dilution buffer is used in place of sample or standard to determine basal clotting time. The timer of the fibrometer (CoA Screener Hemostasis Analyzer, American Labor) is started immediately after the addition of 50 µL 37° C. 30 mM $CaCl_2$ to each sample or standard. Activated protein C concentration in samples are calculated from the linear regression equation of the standard curve. Clotting times are the average of a minimum of three replicates, including standard curve samples. Protein concentrations of recombinant activated protein C was measured by UV 280 nm extinction $E^{0.1\%}=85$.

EXAMPLE 1

Chromatographic Separation of aPC

A solution of aPC having a conductivity of approximately 14 nMho and a pH of 5.7 was applied to a 9.5 cm×9 cm (h×d) column of S-Sepharose Fast Flow cation exchange resin linked in tandem with a 25cm×14 cm (h×d) column of Q Sepharose Fast Flow anion exchange resin. Both columns had been pre-equilibrated in 20 mM sodium citrate, pH 6.0, 150 mM NaCl. The column load was 10 grams of aPC per liter of anion exchange resin. The column was washed with >2 column volumes of equilibration buffer and step-eluted with 20 mM sodium citrate pH 6.0, 400 mM NaCl. All operations were performed at 2–8° C. and at a linear flow rate of 60 cm/hr.

Although the aPC had a high activity (539 units/mg by APTT assay) and was quite concentrated during the chromatography (>20 g/L at peak) and in the aggregate mainstream (10 grams /L), the product remained stable. These observations were confirmed by reduced and non-reduced tryptic digest of the light chain and mass spectrometry, which indicated no detectable (<2%) isoforms containing the 308–309 endoproteolytic clip nor the presence of des (1–9)aPC and des(1–10) (<5%).

EXAMPLE 2

Virus Filtration

Activated protein C (4 mg/mL) in 20 mM Tris, 150 mM NaCl, and 20 mM EDTA buffer is filtered using a tangential flow filtration (Millipore Virusolve™ 180 membrane). Passage of aPC through the filter is facilitated by using a diafiltration buffer. The diafiltration buffer is 20 mm sodium citrate and 150 mM NaCl. A solution (10 L), 4 mg/ml aPC in 20 mM Tris, 150 mM NaCl, and 20 mM EDTA buffer were filtered. The sodium citrate and sodium chloride buffer was used as a diafiltration buffer to yield a final volume of aPC solution of 21.5 L.

EXAMPLE 3

Freeze Drying

A solution is prepared in a vial by adding the appropriate amount of sucrose, sodium chloride, and sodium citrate to a predetermined volume of r-aPC to yield 2.5 mg/mL aPC, 15 mg/mL sucrose, 325 mM sodium chloride and 20 mM sodium citrate at pH 6.0. The solution is lyophilized using a conventional freeze dryer to yield lyophilized aPC vials suitable for reconstitution and administration to a patient. The lyophilized formulations have less than 10% des(1–9) aPC and des(1–10)aPC.

EXAMPLE 4

Freeze Drying

A solution is prepared in a vial by adding the appropriate amount of sucrose, sodium chloride, and sodium citrate to a predetermined volume of r-aPC to yield 5 mg/mL aPC, 30 mg/mL sucrose, 650 mM sodium chloride and 40 mM sodium citrate at pH 6.0. The solution is lyophilized using a conventional freeze dryer to yield lyophilized aPC vials suitable for reconstitution and administration to a patient. The lyophilized formulations have less than 10% des(1–9) aPC and des(1–10)aPC.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A method of processing an aqueous solution of activated protein C, comprising conducting such processing at an ionic strength between about 150 mM and 400 mM and a pH of about 5.7 to about 6.0.

2. The method of claim 1 wherein the activated protein C is human activated protein C.

3. The method of claim 1 wherein the solution comprises sodium chloride.

4. The method of claim 1 wherein the processing is anionic chromatography.

5. The method of claim 4 wherein the pH is buffered with sodium citrate.

6. The method of claim 1 wherein the processing is freeze-drying.

7. The method of claim 1 wherein the processing is filtration.

8. The method of claim 7 wherein the pH is buffered with sodium citrate.

9. The method of claim 1 wherein the activated protein C is recombinantly produced human activated protein C.

10. The method of claim 1 wherein the pH is 6.0.

11. The method of claim 1 wherein the solution comprises a sodium chloride concentration of 325 mM.

12. A method of processing an aqueous solution of recombinantly produced activated protein C, comprising conducting the processing in an aqueous solution having a sodium chloride concentration of 150 mM to 400 mM and a pH of about 5.7 to about 6.0 buffered with sodium citrate; and at a temperature of about 0° C. to about 10° C.

13. The method of claim 12 wherein the pH is 6.0.

14. The method of claim 12 wherein the sodium chloride concentration is 325 mM.

* * * * *

SEQUENCE LISTING

```
<160> NUMBER OF SEQ ID NOS: 2

<210> SEQ ID NO 1
<211> LENGTH: 410
<212> TYPE: PRT
<213> ORGANISM: Homo sapiens

<400> SEQUENCE: 1

His Ser Ser Leu Glu Arg Glu Cys Ile Glu Glu Ile Cys Asp Phe Glu
  1               5                  10                  15

Glu Ala Lys Glu Ile Phe Gln Asn Val Asp Asp Thr Leu Ala Phe Trp
             20                  25                  30

Ser Lys His Val Asp Gly Asp Gln Cys Leu Val Leu Pro Leu Glu His
         35                  40                  45
```

-continued

```
Pro Cys Ala Ser Leu Cys Cys Gly His Gly Thr Cys Ile Asp Gly Ile
     50                  55                  60

Gly Ser Phe Ser Cys Asp Cys Arg Ser Gly Trp Glu Gly Arg Phe Cys
 65                  70                  75                  80

Gln Arg Glu Val Ser Phe Leu Asn Cys Ser Leu Asp Asn Gly Gly Cys
                 85                  90                  95

Thr His Tyr Cys Leu Glu Glu Val Gly Trp Arg Arg Cys Ser Cys Ala
             100                 105                 110

Pro Gly Tyr Lys Leu Gly Asp Asp Leu Leu Gln Cys His Pro Ala Val
             115                 120                 125

Lys Phe Pro Cys Gly Arg Pro Trp Lys Arg Met Glu Lys Lys Arg Ser
     130                 135                 140

His Leu Lys Arg Asp Thr Glu Asp Gln Glu Asp Gln Val Asp Pro Arg
145                 150                 155                 160

Leu Ile Asp Gly Lys Met Thr Arg Arg Gly Asp Ser Pro Trp Gln Val
                165                 170                 175

Val Leu Leu Asp Ser Lys Lys Lys Leu Ala Cys Gly Ala Val Leu Ile
            180                 185                 190

His Pro Ser Trp Val Leu Thr Ala Ala His Cys Met Asp Glu Ser Lys
     195                 200                 205

Lys Leu Leu Val Arg Leu Gly Glu Tyr Asp Leu Arg Arg Trp Glu Lys
210                 215                 220

Trp Glu Leu Asp Leu Asp Ile Lys Glu Val Phe Val His Pro Asn Tyr
225                 230                 235                 240

Ser Lys Ser Thr Thr Asp Asn Asp Ile Ala Leu Leu His Leu Ala Gln
                245                 250                 255

Pro Ala Thr Leu Ser Gln Thr Ile Val Pro Ile Cys Leu Pro Asp Ser
            260                 265                 270

Gly Leu Ala Glu Arg Glu Leu Asn Gln Ala Gly Gln Glu Thr Leu Val
     275                 280                 285

Thr Gly Trp Gly Tyr His Ser Ser Arg Glu Lys Glu Ala Lys Arg Asn
290                 295                 300

Arg Thr Phe Val Leu Asn Phe Ile Lys Ile Pro Val Val Pro His Asn
305                 310                 315                 320

Glu Cys Ser Glu Val Met Ser Asn Met Val Ser Glu Asn Met Leu Cys
                325                 330                 335

Ala Gly Ile Leu Gly Asp Arg Gln Asp Ala Cys Glu Gly Asp Ser Gly
            340                 345                 350

Gly Pro Met Val Ala Ser Phe His Gly Thr Trp Phe Leu Val Gly Leu
     355                 360                 365

Val Ser Trp Gly Glu Gly Cys Gly Leu Leu His Asn Tyr Gly Val Tyr
370                 375                 380

Thr Lys Val Ser Arg Tyr Leu Asp Trp Ile His Gly His Ile Arg Asp
385                 390                 395                 400

Lys Glu Ala Pro Gln Lys Ser Trp Ala Pro
                405                 410
```

<210> SEQ ID NO 2
<211> LENGTH: 409
<212> TYPE: PRT
<213> ORGANISM: Homo sapiens

<400> SEQUENCE: 2

```
Ser Ser Leu Glu Arg Glu Cys Ile Glu Glu Ile Cys Asp Phe Glu Glu
 1               5                  10                  15
```

-continued

```
Ala Lys Glu Ile Phe Gln Asn Val Asp Asp Thr Leu Ala Phe Trp Ser
             20                  25                  30

Lys His Val Asp Gly Asp Gln Cys Leu Val Leu Pro Leu Glu His Pro
         35                  40                  45

Cys Ala Ser Leu Cys Cys Gly His Gly Thr Cys Ile Asp Gly Ile Gly
     50                  55                  60

Ser Phe Ser Cys Asp Cys Arg Ser Gly Trp Glu Gly Arg Phe Cys Gln
 65                  70                  75                  80

Arg Glu Val Ser Phe Leu Asn Cys Ser Leu Asp Asn Gly Gly Cys Thr
                 85                  90                  95

His Tyr Cys Leu Glu Glu Val Gly Trp Arg Arg Cys Ser Cys Ala Pro
            100                 105                 110

Gly Tyr Lys Leu Gly Asp Asp Leu Leu Gln Cys His Pro Ala Val Lys
        115                 120                 125

Phe Pro Cys Gly Arg Pro Trp Lys Arg Met Glu Lys Lys Arg Ser His
    130                 135                 140

Leu Lys Arg Asp Thr Glu Asp Gln Glu Asp Gln Val Asp Pro Arg Leu
145                 150                 155                 160

Ile Asp Gly Lys Met Thr Arg Arg Gly Asp Ser Pro Trp Gln Val Val
                165                 170                 175

Leu Leu Asp Ser Lys Lys Lys Leu Ala Cys Gly Ala Val Leu Ile His
            180                 185                 190

Pro Ser Trp Val Leu Thr Ala Ala His Cys Met Asp Glu Ser Lys Lys
        195                 200                 205

Leu Leu Val Arg Leu Gly Glu Tyr Asp Leu Arg Arg Trp Glu Lys Trp
    210                 215                 220

Glu Leu Asp Leu Asp Ile Lys Glu Val Phe Val His Pro Asn Tyr Ser
225                 230                 235                 240

Lys Ser Thr Thr Asp Asn Asp Ile Ala Leu Leu His Leu Ala Gln Pro
                245                 250                 255

Ala Thr Leu Ser Gln Thr Ile Val Pro Ile Cys Leu Pro Asp Ser Gly
            260                 265                 270

Leu Ala Glu Arg Glu Leu Asn Gln Ala Gly Gln Glu Thr Leu Val Thr
        275                 280                 285

Gly Trp Gly Tyr His Ser Ser Arg Glu Lys Glu Ala Lys Arg Asn Arg
    290                 295                 300

Thr Phe Val Leu Asn Phe Ile Lys Ile Pro Val Val Pro His Asn Glu
305                 310                 315                 320

Cys Ser Glu Val Met Ser Asn Met Val Ser Glu Asn Met Leu Cys Ala
                325                 330                 335

Gly Ile Leu Gly Asp Arg Gln Asp Ala Cys Glu Gly Asp Ser Gly Gly
            340                 345                 350

Pro Met Val Ala Ser Phe His Gly Thr Trp Phe Leu Val Gly Leu Val
        355                 360                 365

Ser Trp Gly Glu Gly Cys Gly Leu Leu His Asn Tyr Gly Val Tyr Thr
    370                 375                 380

Lys Val Ser Arg Tyr Leu Asp Trp Ile His Gly His Ile Arg Asp Lys
385                 390                 395                 400

Glu Ala Pro Gln Lys Ser Trp Ala Pro
                405
```